United States Patent
Strickler et al.

(10) Patent No.: US 8,163,948 B2
(45) Date of Patent: *Apr. 24, 2012

(54) PROCESSES FOR PRODUCING TRANSITION METAL AMIDO AND IMIDO COMPOUNDS

(75) Inventors: Jamie R. Strickler, Baton Rouge, LA (US); Feng-Jung Wu, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/919,629

(22) PCT Filed: Mar. 2, 2009

(86) PCT No.: PCT/US2009/035711

§ 371 (c)(1),
(2), (4) Date: Aug. 26, 2010

(87) PCT Pub. No.: WO2009/108930

PCT Pub. Date: Sep. 3, 2009

(65) Prior Publication Data

US 2010/0331562 A1    Dec. 30, 2010

Related U.S. Application Data

(60) Provisional application No. 61/032,810, filed on Feb. 29, 2008.

(51) Int. Cl.
*C07F 9/00* (2006.01)
*C07F 7/00* (2006.01)
*C07F 15/00* (2006.01)

(52) U.S. Cl. ............. 556/42; 556/51; 556/136; 556/138
(58) Field of Classification Search ............... 556/42, 556/51, 136, 138
See application file for complete search history.

(56) References Cited

U.S. PATENT DOCUMENTS

2010/0204499 A1\* 8/2010 Strickler et al. ................ 556/42

FOREIGN PATENT DOCUMENTS

| WO | 2004011692 A2 | 2/2004 |
| WO | 2005038866 A2 | 4/2005 |
| WO | 2009032970 A2 | 3/2009 |

OTHER PUBLICATIONS

Hans Bürger, et al; "Titan-Stickstoff-Verbindungen VII. Darstellung, IR-, Raman- und 1H-KMR-Spektren von tris (dialkylamino)titanalkylen"; Journal of Organometallic Chemistry: Nov. 1969; p. 129-139; vol. 20; Issue 1: Elsevier Science B.V.; Amsterdam, Netherlands.

\* cited by examiner

*Primary Examiner* — Porfirio Nazario Gonzalez
(74) *Attorney, Agent, or Firm* — James A. Jubinsky

(57) ABSTRACT

Processes are provided for producing transition metal amidos and/or imidos. In methods according to this invention, at least one halogenated transition metal, an amine compound and a solvent are combined, followed by the addition of an alkylated metal or a Grignard reagent to produce the transition metal amide and/or imido.

12 Claims, No Drawings

PROCESSES FOR PRODUCING TRANSITION METAL AMIDO AND IMIDO COMPOUNDS

BACKGROUND

Metal amides are useful as precursor compounds for chemical vapor deposition; see, e.g., U.S. Pat. Nos. 5,178, 911; 5,417,823, and 6,080,446, Metal amides are also useful in the synthesis of polymerization catalysts; see, e.g., U.S. Pat. No. 6,020,444. Metal amides are also useful in formation of metal-rich layers or materials having high dielectric constants, such as are used, in construction of microelectronic devices; see, e.g., WO 02/27063. Metal imido compounds are useful as Zieglar-Natta olefin metathesis polymerization catalysts; see, e.g., U.S. Pat. No. 5,405,924.

Many known processes for making metal amides and/or metal imidos require the transfer of a solid transition metal salt to a slurry of a lithium alkylamide. See, e.g., D. C. Bradley and I. M. Thomas, J. Chem. Soc., 1960, 3857-3861. The addition of solids into a reaction vessel with a reactive reagent present is a difficult and potentially hazardous operation on commercial scale since the flow is hard to control. The reverse reaction (i.e., adding a lithium amide to a metal halide slurry) is also possible, however the lithium amide salts are usually of low solubility and slurries of these salts tend to be nonhomogeneous, thick and difficult to completely transfer, and thus reaction stoichiometry cannot he adequately controlled to provide metal amides and imidos of commercially acceptable quality and quantity. The reverse addition also requires the use of a second vessel for processing and is therefore less desirable.

U.S. Pat. No. 7,238,821 discloses a method tor making large scale organometallic compounds, including transition metal amides, via a one-pot process wherein (i) a hydrocarbon or hetereatom-containing material, such as an amine, is reacted with a base material, such as butyl-lithium, in the presence of a solvent, to produce a first reaction mixture, (ii) a metal source is added to the first reaction mixture, (iii) the hydrocarbon or heteroatom-containing material is reacted with the metal source to produce a second reaction mixture comprising the organometallic compound, and (iv) the organometallic compound is separated from the second reaction mixture. In the reference D. C. Bradley and I. M. Thomas, J. Chem. Soc, 1960, 3857-3861, the same process is disclosed at page 3860 wherein, butyllithium, produced from n-butyl bromide and lithium, and diethylamide are combined form a first reaction mixture, to which a metal compound and solvent are added. The first reaction mixture is caused to react such that a second reaction mixture is formed comprising a metal amide, which is subsequently separated from the second reaction mixture.

Despite advancements in the synthesis of metal amides and imidos, there is a continuing need to develop more efficient and lower cost processes.

THE INVENTION

This invention meets the above-described need by providing methods of producing a metal amide and/or metal imidos comprising (i) combining in a first reaction mixture at lest one halogenated transition metal, an amine composition, and a solvent, (ii) subsequently adding to at least a portion of the first reaction mixture an alkylated metal or a Grignard reagent thereby forming a second reaction mixture, and (iii) subjecting the second reaction mixture to reaction conditions sufficient to produce a transition metal amido or imido compound, wherein the amine composition comprises at least one primary amine, or at least one secondary amine, or at least one diamine, or mixtures thereof. Optionally, the amine composition can further comprise a tertiary amine.

The alkylated metal or the Grignard reagent can be in liquid form and can be added directly to the first reaction mixture. Thus, this invention also provides one-pot methods of producing a metal amide comprising (i) combining in a first reaction mixture at least one halogenated transition metal, an amine composition, and a solvent, (ii) subsequently adding an alkylated metal or a Grignard reagent to the first reaction mixture, and (iii) following the addition of the alkylated metal or a Grignard reagent to the first reaction mixture, subjecting the first reaction mixture to reaction conditions sufficient to produce a transition metal amido or imido compound, wherein the amine composition comprises at least one primary amine, at least one secondary amine, at least one diamine, or mixtures thereof. Optionally, the amine composition can further comprise a tertiary amine.

Also provided are methods of producing a transition metal amide, comprising (i) combining at least one halogenaied transition metal, an amine, composition, and a solvent to produce a first intermediate composition, (ii) optionally removing an amine hydrohalide from the first intermediate composition, (iii) combining a portion of the first intermediate composition and an alkylated metal or a Grignard reagent to produce a second intermediate composition, and (iv) combining at least a portion of the second intermediate composition and an alkylated metal or the Grignard reagent to produce the transition metal amido or imido, wherein the amine composition comprises at least one primary amine, or at least one secondary amine, or at least one diamine, or mixtures thereof. Optionally, the amine composition can further comprise a tertiary amine.

The halogenated transition metals suitable for use in this invention may comprise scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalam, tungsten, rhenium, osmium, iridium, platinum, gold, mercury, lanthanum, uranium, rutherfordium, dubnium, seaborgium, bohrium, hassium, meitnerium, unumnilium, unununium, ununbium, and the like. Such halogenated transition metals must comprise at least one halogen atom, e.g., fluorine, chlorine, bromine, or iodine, and normally and preferably, all halogen atoms are the same. Generally, the halogenated transition metal has the formula $M^1X^1_n$ where $M^1$ is a transition metal atom and $X^1$ is independently a halogen atom, a cyclopentadienyl, an indenyl, a fluorenyl, an alcohol, a substituted phenol, or the like, provided that at least one $X^1$ is a halogen atom, and n is the valence of $M^1$. Such halogenated transition metals are readily available commercially, and include titanium tetrafluoride, titanium tetrachloride, titanium tetrabromide, titanium iodide, zirconium tetrafluoride, zirconium tetrachloride, zirconium tetrabromide, zirconium iodide, hafnium tetrafluoride, hafnium tetrachloride, hafnium tetrabromide, hafnium iodide, tantalum tetrafluoride, tantalum tetrachloride, tantalum tetrabromide, and tantalum iodide. Preferably, the metal is hafnium, titanium, tantalum or zirconium. The halogen atom is preferably a chlorine, bromine, or iodine atom, more preferably, the halogen atom is a chlorine or bromine atom.

Amines that can be used in this invention have hydrocarbyl groups that may be the same or different, and each hydrocarbyl group has, independently, from 1 to about 20 carbon atoms. Preferably, each hydrocarbyl group has from 1 to about 12 carbon atoms and more preferably from 1 to about 5 carbon atoms. Hydroearbyi groups can also include cyclic hydrocarbyl groups. Non-limiting examples of amines include dimethylamine, ethylmethylamine, diethylamine, cyclopentylamine, tert-butylamine, ethylamine, and the like.

The halogenated transition metal may be brought together with the amine as a solid, or in a mixture with a suitable solvent. For the bringing together of the transition metal halide and the amine composition, the solvent can be any aprotic compound in which the reactants and reaction products are stable. Examples include one or more alkanes, aromatic hydrocarbons, hydrocarbylaromatic hydrocarbons, ethers, or mixtures thereof, that are liquid at the conditions at which the addition is conducted. Suitable solvents include pentane, cyclopentane, hexane, cyclohexane, methylcyclohexane, cyclohexene, heptane, cycloheptane, octane, isooctane, cyclooctane, cyclooctadiene, nonane, benxene, toluene, xylene, dimethyl ether, diethyl ether, di-n-propyl ether, ethyl-n-propyl ether, diisopropyl ether, text-butyl ethyl ether, di-n-butyl ether, diheptyl ether, oxetane, tetrahydrofuran, methyltetrahydrofuran, 1,4-dioxane, 1,3-dioxane, cyclohexylmethyl ether, ethylene glycol dimethyl ether and the like.

Alkylated metals suitable for use in this invention include compounds having the formula $M^2R^3$ or $M^2R^3_2$ wherein $M^2$ can be any suitable non-transition metal in groups 1 or 2, e.g., lithium, beryllium, sodium, magnesium, and $R^3$ is a hydrocarbyl group having 1 to about 20 carbon atoms.

Grignard reagents suitable for use in this invention include alkyl and aryl magnesium halides having the formula $R^4MgX^2$ wherein $R^4$ is an alkyl or aryl group having from 1 to about 20 carbon atoms, Mg is magnesium, and $X^2$ is a halogen atom.

In methods of this invention, the halogenated transition metal can he combined in a stoichiometric amount as to the total amide or imido desired. It is preferred that a slight excess of amine compound be used. An equimolar amount of amine compound is about one mole of amine compound for each mole of halide ligand. For example, when the halogenated transition metal is zirconium chloride, four or more equivalents of methyl ethyl amine can be used to make $Zr(NEtMe)_4$. Thus, four moles of amine compound for each mole of transition metal is considered to be the equimolar amount.

During the bringing together of the halogenated transition metal and the amine compound, the reaction temperature is preferably kept low, cooling is often necessary to maintain the low temperature because the reaction is exothermic. Reaction pressure is not critical and is generally maintained under a slight positive pressure in an inert atmosphere. The reaction temperature will depend upon and range between the freezing points and boiling points of the reaction mixture components. Preferably, the temperatures are no higher than about 40° C., more preferably, the temperature is no higher than about 20° C. The temperature is most preferably no higher than about 10° C. Allowing the temperature to rise above about 60° C. is believed to increase the rate of the side reactions.

Without wishing to he bound by theory, it is believed that the halogenated transition metal must be in close proximity to an amine compound tor the process to be successful. The addition of the amine to the transition metal prior to addition of the base provides this close proximity through formation of a complex between the transition metal and one or more amines. Mixing during the bringing together of the halogenated transition metal and the amine compound is important to avoid locally high concentrations of halogenated transition metal (and thus locally low concentrations of amine).

Upon addition of the alkylated metal or Grignard reagent to the reaction mixture, the reaction mixture is preferably kept at a low temperature during the addition the alkylated metal or Grignard reagent, and the addition is performed in a controlled manner. The rate of addition is dictated by the exotherm of the reaction mixture, such that the temperature of the reaction mixture is maintained below about ambient temperature, preferably below about 20° C., more preferably below about 10° C. After the addition of the alkylated metal or Grignard reagent is complete, the reaction mixture is preferably allowed to warm to ambient temperature under constant mixing, which may be maintained from about 30 min to about 24 hours, and additionally may be heated to a temperature above ambient temperature for sufficient time to ensure complete reaction. As stated above, reaction pressure is not critical and is generally maintained under a slight positive pressure in an inert atmosphere.

Again, without wishing to be bound by theory, it is believed that an intermediate composition is formed upon the reaction of the halogenated transition metal and amine in the first reaction mixture, wherein the intermediate composition has the formula $M^1X^1_{(n-x)}(NR^1R^2)_x \bullet y(R^1R^2NH)$, wherein n is the valence of $M^1$, x is less than or equal to the maximum oxidation state of $M^1$, and y is from about 0 to about 2. $M^1$ is a transition metal atom, $X^1$ is a halogen atom, a cyclopentadienyl, an indenyl, a fluorenyl, an alcohol, a substituted phenol, or the like, provided that at least one $X^1$ is a halogen atom, and each of $R^1$ and $R^2$ is independently an hydrocarbyl group having from 1 to about 20 carbon atoms.

EXAMPLES

The following examples are illustrative of the principles of this invention. It is understood that this invention is not limited to any one specific embodiment exemplified herein, whether in the examples or the remainder of this patent application.

Example 1

Preparation of $Hf(NEtMe)_4$ $HfCl_4$ (2.00 g) was slurried in 18.2 g of anhydrous toluene. Ethylmethylamine (1.70 g) was added and a cloudy yellow solution formed. The reaction was then cooled in an ice-water bath and n-BuLi in hexanes was added (2.5M, 10.5 mL). The slurry was allowed to warm to ambient temperature for 3 hours and then heated to 50-55° C. for 3 hours. The white solids were filtered on a medium frit. The volatiles were removed from the yellow filtrate at 50° C. with vacuum. The isolated yellow oily liquid was determined to be pure Hf(NMeEt)$_4$. The yield was 2.19 g (85%).

Example 2

Preparation of t-BuN=Ta(NEtMe)$_3$ $TaCl_5$ (4.00 g) was slurried in 45.2 g of toluene. A yellow slurry resulted. Ethylmethylamine (2.70 g) was added and a red-orange solution with some crystalline solids formed. After 20 minutes, t-BuNH$_2$ (0.82 g) was added and the reaction mixture changed to yellow over 30 minutes. The reaction was then cooled in an ice-water bath and nBuLi in hexanes were added (2.5M, 22.5 mL), A yellow slurry formed. The slurry was allowed to warm to ambient temperature and to stir overnight. The white solids were filtered on a medium frit. The volatiles were removed from the amber filtrate at 40° C. with vacuum. The t-BaN=Ta(NEtMe)$_3$ was isolated as a viscous amber liquid.

Example 3

Preparation of Zr(NEtMe)$_4$

ZrCl$_4$ (3.59 g) was slurried in 28.2 g of anhydrous toluene. Ethylmethylamine (4.14 g) was added to the ZrCl$_4$ at ambient temperature. A cloudy yellow solution formed. After stirring overnight, the reaction had not changed. The solution was kept under a nitrogen atmosphere and cooled in an ice-water bath. n-BuLi in hexanes was added (2.5M, 23 mL) over 30 minutes. The slurry was allowed to warm to ambient temperature and to stir for 4 hours. An aliquot was removed, diluted with deuterobenzene, and filtered. A $^1$H NMR showed complete conversion to Zr(NEtMe)$_4$. Dried Celite was added to the reaction (1.52 g) and a roughly equivalent amount was placed on top of a 30 mL coarse frit. A clear orange-yellow filtrate was obtained. The toluene was removed in vacuo. The orange liquid which remained weighed 4.99 g and was determined, to be 4.99 g (83%) of Zr(NMeEt)$_4$.

Example 4

Preparation of Hf(NEtMe)$_4$

HfCl$_4$ (2.00 g) was slurried in 17.0 g of anhydrous toluene. Ethylmethylamine (1.7 g) was added and a cloudy yellow solution formed. The reaction was then cooled in an ice-water bath and EtMgCl in diethylether was added (2.0M, 12.5 mL). A gelatinous slurry formed. The slurry was allowed to warm to ambient temperature and stirred overnight The viscous slurry was filtered on a Celite covered frit. The gelatinous solids were washed with 11 g of toluene. The filtrates were combined and analyzed by $^1$H NMR. Approximately 15% Hf(NMeEt)$_3$Cl remained. An additional 0.19 g of HNEtMe and then 0.6 mL of EtMgCl solution were added at ambient temperature. After stirring for 4 h, the reaction was analyzed using $^1$H NMR and the conversion to product was complete. The volatiles were removed and then 5.2 g of toluene was added back to the oily solid. The insoluble material was filtered on a coarse frit. The reddish-orange filtrate weighed 5.49 g and was 16.1 wt % Hf(NMeEt)$_4$ (34% yield).

Example 5

Ti(NEt$_2$)$_4$

To a cold solution of HNBb (29.3 g, 400 mmol) in hexanes (71 g) in an ice/acetone bath was added dropwise a solution of TiCl$_4$ (9.48 g, 50 mmol) in hexane (20 g). The rate of the addition was adjusted so that die temperature of the solution was kept between −2 to 2° C. The addition lasted about 30 minutes and alter that the resulting red slurry was allowed to return to room temperature slowly. The slurry was filtered via a medium frit and the white solids (H$_2$NEt$_2$Cl) was washed with 20 g hexanes. The collected ammonium chloride after drying weighed 11.9 g. The combined filtrate weighed 138 g. According to the weight of the ammonium chloride produced, the weighted empirical formula of the Ti products is calculated to be roughly Ti(NEt$_2$)$_{2.2}$Cl$_{1.8}$.

A half Of the deep red hexane solution of Ti(NEt$_2$)$_{2.2}$Cl$_{1.8}$ from above (69 g, 25 mmol Ti) was cooled in an ice/acetone batk A 25.4 wt % solution of n-Buli in hexanes (11.35 g, 45 mmol) was then added. During the addition, which lasted about 20 minutes, the red solution turned into a green slurry gradually. After returning to room temperature, the slurry was allowed to stir overnight. The next day, the slurry was filtered via a medium frit with some filter-aid. The filtered solids were washed with hexanes (~10 ml) until colorless. The combined orange filtrate, weighed 63.1 g. The solution was quantitatively analyzed by the 1H NMR which showed the yield of Ti(NEt$_2$)$_4$ being 68.4%. The solution was then stripped off solvents in vacuo, leaving a deep red oily residue weighing 5.96 g.

Example 6

Hf(NMe$_2$)$_4$

A light yellow hazy solution of HfCl$_4$ (7.21 g, 22.5 mmol) and HNMe$_2$ (5.80 g, 129 mmol) in THF (20 g) and isohexane (40 g) was cooled in an ice/acetone bath. To this solution was added dropwise a 25.4 wt % of n-BuLi in hexanes (22.7 g, 90 mmol) over a period of 40 minutes. After that the cold bath was removed and the solution was heated in an oil hath to 54° C. for 3 hours. After cooling, the resulting slurry was filtered via a medium frit with some filter-aid and the solids were washed with 10 g of a 2:1 isohexane/THF mixture. The combined filtrate weighed 79.9 g, which was analysed quantitatively by the 1H NMR showed a 74.4% contained yield of Hf(NMe$_2$)$_4$. The solvent was stripped off in vacuo and after that the yellow oily residue was vacuum distilled at 70-80° C./2-5 mmMg to give a white solid weighing 5.79 g a 72.5% yield.

Example 7

Hf(NEt$_2$)$_4$

To a 250 ml three-neck round bottom flask was charged HfCl$_4$ (7.21 g, 22.5 mmol) and 40 g toluene to give a light yellow slurry. After cooling the slurry to −13° C., 10 g of DME was added q sickly with stirring which caused the temperature to rise to 8° C. and produced a thicker white slurry. The slurry was again cooled to −17° C. and then MeEtNH (8.30 g, 113 mmol) was added quickly with stirring which caused the temperature to rise to −2° C. and produced a colorless clear solution. The resulting HfCl$_4$/toluene/DME/MeEtNH solution was cooled in a −10 to −20° C. bath and n-BuLi in hexanes (24.7 wt %, 23.4 g, 90 mmol) was added dropwise. The rate of the addition was dictated by keeping the solution temperature below 10° C. The addition took about 20 min to complete. The resulting slurry was allowed to warm and was stirred for 2 hours before a sample was withdrawn for 1H NMR analysis to confirm the reaction was complete. The resulting white slurry was then filtered via a medium frit to remove LiCl, and the solids were washed with 7 g of toluene. The combined pale yellow filtrate, weighing about 92 g, was stripped of volatiles under 5-10 torr vacuum and a final temperature of 64° C. The residual yellow cloudy liquid weighed 10.7 g, which was subjected to distillation at 3 torrs/132° C. to afford a colorless liquid of 9.02 g, a 85.8% yield.

Processes according to this invention are particularly advantageous in that they allow for production of transition metal amides or imides in one pot reactions that are equipment and time efficient; do not require expensive ether solvents; do not require slurry transfers (which can be time consuming and lead to reagent stoichiometry problems); and further, the reaction end point can be titrated giving optimum yields (avoids byproducts and waste of expensive alkyl lithium).

It is to be understood that the reactants and components referred to by chemical name or formula anywhere in the specification or claims hereof whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identify through a chemical reaction or transformation during the course of contacting, combining, blending or mixing operations, if conducted in accordance, with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

The invention claimed is:

1. A method for producing a transition metal amido and/or imido comprising (i) combining in a first reaction mixture at least one halogenated transition metal, an amine composition, and a solvent, (ii) subsequently adding to at least a portion of the first reaction mixture an alkylated metal or a Grignard reagent thereby forming a second reaction mixture, and (iii) subjecting the second reaction mixture to reaction conditions sufficient to produce the transition metal amido and/or imido, wherein the amine composition comprises at least one primary amine, at least one secondary amine, at least one diamine, or mixtures thereof.

2. A one-pot method for producing a transition metal amido and/or imido comprising (i) combining in a first reaction mixture at least one halogenated transition metal, an amine composition, and a solvent, (ii) subsequently adding an alkylated metal or a Grignard reagent to the first reaction mixture, and (iii) following the addition of the alkylated metal or a Grignard reagent to the first reaction mixture, subjecting the first reaction mixture to reaction conditions sufficient to produce the transition metal amido and/or imido, wherein the amine composition comprises at least one primary amine, at least one secondary amine, at least one diamine, or mixtures thereof.

3. A method of producing a transition metal amido and/or imido, comprising (i) combining at least one halogenated transition metal, an amine composition, and a solvent to produce a first intermediate composition, (ii) optionally removing an amine hydrohalide from the first intermediate composition, (iii) combining a portion of the first intermediate composition and an alkylated metal or a Grignard reagent to produce a second intermediate composition, and (iv) combining at least a portion of the second intermediate composition and an alkylated metal or the Grignard reagent to produce the transition metal amido and/or imido, wherein the amine composition comprises at least one primary amine, at least one secondary amine, at least one diamine, or mixtures thereof.

4. The method of claim 1 wherein the transition metal is hafnium, titanium, tantalum, or zirconium, and the halogen is chlorine, bromine, or iodine.

5. The method of claim 1 wherein the halogenated transition metal has the formula $M^1X^1_n$, where $M^1$ is a transition metal atom and $X^1$ is independently a halogen atom, a cyclopentadienyl, an indenyl, a fluorenyl, an alcohol, or a substituted phenol, provided that at least one $X^1$ is a halogen atom, and n is the valence of $M^1$.

6. The method of claim 1 any of the preceding claims wherein the amine compound comprises one or more hydrocarbyl groups having from 1 to about 20 carbon atoms.

7. The method of claim 1 wherein the alkylated metal has the formula $M^2R^3$ or $M^2R^3_2$ wherein $M^2$ is a non-transition metal in Groups 1 or 2, and $R^3$ is a hydrocarbyl group having 1 to about 20 carbon atoms.

8. The method of claim 1 wherein the Grignard reagent is an alkyl or aryl magnesium halide having the formula $R^4MgX^2$ wherein $R^4$ is an alkyl or aryl group having from 1 to about 20 carbon atoms, Mg is magnesium, and $X^2$ is a halogen atom.

9. The method of claim 1 wherein a molar excess of amine compound with respect to transition metal halide is employed.

10. The method of claim 1 wherein the temperature of step (i) is no higher than about 40° C.

11. The method of claim 1 wherein the temperature subsequent to and during the addition of the alkylated metal or Grignard reagent is maintained below about ambient temperature.

12. The method of claim 1 wherein after the addition of the alkylated metal or Grignard reagent is complete, the reaction mixture is allowed to increase under constant mixing, which is maintained for from about 30 min to about 24 hours.

* * * * *